(12) United States Patent
Schick et al.

(10) Patent No.: US 8,231,267 B2
(45) Date of Patent: Jul. 31, 2012

(54) CALORIMETER AND METHODS OF USING IT AND CONTROL SYSTEMS THEREFOR

(75) Inventors: Christoph E. G. Schick, Sanitz (DE); Evgeny Zhuravlev, Rostock (DE)

(73) Assignee: PerkinElmer Health Sciences, Inc., Waltham, MA (US)

(*) Notice: Subject to any disclaimer, the term of this patent is extended or adjusted under 35 U.S.C. 154(b) by 334 days.

(21) Appl. No.: 12/479,105

(22) Filed: Jun. 5, 2009

(65) Prior Publication Data
US 2010/0046573 A1    Feb. 25, 2010

Related U.S. Application Data

(60) Provisional application No. 61/059,321, filed on Jun. 6, 2008.

(51) Int. Cl.
*G01K 17/08* (2006.01)
*G01N 25/20* (2006.01)
(52) U.S. Cl. .............. 374/31; 374/10; 374/11
(58) Field of Classification Search ........... 374/10–12, 374/31, 33
See application file for complete search history.

(56) References Cited

U.S. PATENT DOCUMENTS

| | | | |
|---|---|---|---|
| 3,675,465 A * | 7/1972 | Sommer et al. ............. | 374/11 |
| 4,821,303 A | 4/1989 | Fawcett et al. | |
| 5,672,289 A * | 9/1997 | O'Neill ..................... | 219/497 |
| 5,842,788 A | 12/1998 | Danley et al. | |
| 5,852,166 A | 12/1998 | Gruber et al. | |
| 6,170,984 B1 * | 1/2001 | Schawe et al. ............... | 374/10 |
| 6,530,686 B1 * | 3/2003 | Nakamura .................. | 374/11 |
| 6,632,015 B2 * | 10/2003 | Nagasawa ................. | 374/11 |
| 2007/0189357 A1 | 8/2007 | Nishimura | |

OTHER PUBLICATIONS

Adamovsky et al., "Ultr-fast Isothermal Calorimetry Using Thin Film Sensors", Thermochimica Acta, vol. 415, 2004, pp. 1-7.
Brunel et al., "A New Software to Show the Behaviour of the PID Controller. Influence of the Setting Parameters of DSCs. Part 1." Journal of Thermal Analysis and Calorimetry, vol. 59, No. 3, Mar. 2000, pp. 999-7015.
Van Herwaarden, "Overview of Calorimeter Chips for Various Applications," Thermochimica Acta, vol. 432, 2005, pp. 192-201.

* cited by examiner

*Primary Examiner* — Amy Cohen Johnson
(74) *Attorney, Agent, or Firm* — Lando & Anastasti, LLP

(57) ABSTRACT

Control systems and calorimeters using them are provided. In certain examples, a calorimeter comprising a thin film sample sensor, a thin film reference sensor, a first controller configured to receive a temperature signal from only the reference sensor and to generate a first control signal, based on the received temperature signal, to provide average power to the sample sensor and to the reference sensor, and a second controller configured to receive temperature signals from both the sample sensor and the reference sensor and to generate a second control signal, based on the temperature signals received from both the sample sensor and the reference sensor, to provide differential power to only the sample sensor is described. Methods using the control systems and calorimeters are also described.

16 Claims, 11 Drawing Sheets

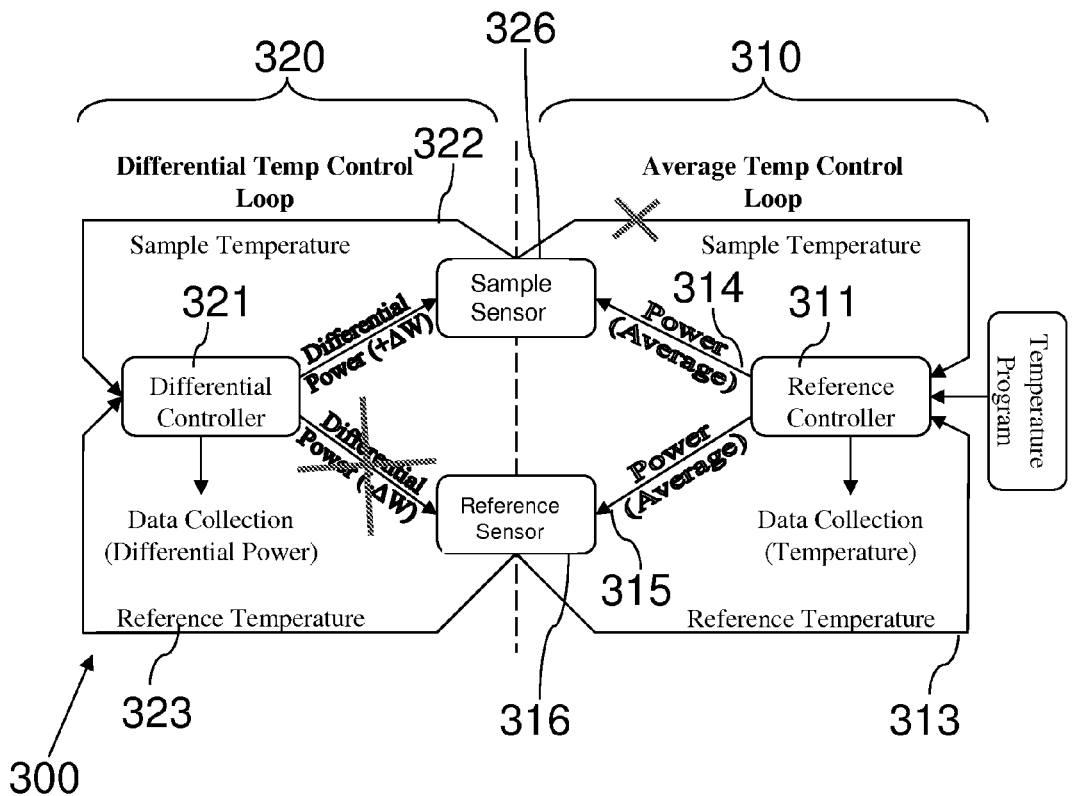
FIG. 3
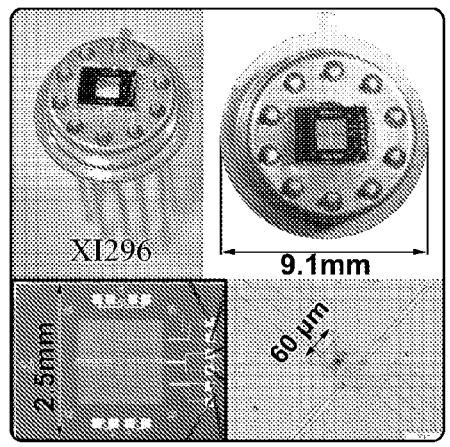
FIG. 4A
FIG. 4B
FIG. 4C
FIG. 4D

CALORIMETER AND METHODS OF USING IT AND CONTROL SYSTEMS THEREFOR

PRIORITY APPLICATION

This application claims priority to U.S. Provisional Application No. 61/059,321 filed on Jun. 6, 2008, the entire disclosure of which is hereby incorporated herein by reference for all purposes.

TECHNOLOGICAL FIELD

Certain examples of the technology described herein are directed to a calorimeter. More particularly, in certain embodiments, a differential scanning calorimeter configured to scan at high heating and cooling rates is described.

BACKGROUND

A calorimeter is a device that performs quantitative measurements of the heat required or evolved during a chemical or physical process. Calorimeters may be used, for example, to measure heat capacities, the heats of reaction that may be produced (exothermic) or consumed (endothermic). A calorimeter may also be used to measure physical transitions including, but not limited to, phase changes, crystallization processes and the like.

SUMMARY

In one aspect, a calorimeter is provided. In certain examples, the calorimeter may comprise a thin film sample sensor, a thin film reference sensor, a first controller configured to receive a temperature signal from only the reference sensor and to generate a first control signal, based on the received temperature signal, to provide average power to the sample sensor and to the reference sensor, and a second controller configured to receive temperature signals from both the sample sensor and the reference sensor and to generate a second control signal, based on the temperature signals received from both the sample sensor and the reference sensor, to provide differential power to only the sample sensor.

In certain embodiments, the first controller is a proportional-integral-derivative controller. In some examples, the second controller is an analog proportional controller or, in certain instances, a proportional-integral-derivative controller. In some examples, the first and second controller can be the same controller. For example, the controller can include a first control loop configured to receive a temperature signal from the reference sensor, e.g., from only the reference sensor. The controller can generate a first control signal, based on the received temperature signal, to provide average power to the sample sensor and to the reference sensor. The controller can also include a second control loop configured to receive temperature signals from both the sample sensor and the reference sensor. The controller can generate a second control signal, based on the temperature signals received from both the sample sensor and the reference sensor, to provide differential power to the sample sensor, e.g., provide differential power to only the sample sensor. In other examples, the calorimeter may further comprise a storage medium configured with a temperature program with a selected heating rate and/or cooling rate. In some embodiments, the heating rate of the temperature program may be at least 10 Kelvin/second. In certain examples, each of the thin film sample sensor and the thin film reference sensor can be a XI-296, a XI-270, a XI-272 or a XI-292 sensor. In some examples, the proportional controller may be configured to detect temperature changes at a heating rate of 10 Kelvin/second or more.

In an additional aspect, a control system for a calorimeter comprising a sample sensor and a reference sensor, the control system comprising a first controller configured to receive a temperature signal from only the reference sensor and to generate a first control signal, based on the received temperature signal, to provide power to the sample sensor and to the reference sensor, and a second controller configured to receive temperature signals from both the sample sensor and the reference sensor and to generate a second control signal to provide differential power to only the sample sensor is disclosed.

In certain embodiments, the first controller may be a proportional-integral-derivative controller and the second controller is an analog proportional controller. In certain examples, the first controller and the second controller may each be configured to provide power to a thin film sample sensor and a thin film reference sensor. In some examples, the second controller may be configured to detect temperature changes at a heating rate of 10 Kelvin/second or more.

In another aspect, a method of controlling a calorimeter that includes a reference sensor and a sample sensor is disclosed. In certain examples, the method comprises generating a first control signal using a first controller, the first control signal based on receipt of a temperature signal from only the reference sensor of the calorimeter by the first controller. In some examples, the method may further comprise providing power to the reference sensor and the sample sensor, based the generated first control signal, to control the average temperature of the reference sensor and the sample sensor. In other examples, the method may further comprise generating a second control signal using a second controller, the second control signal based on receipt of a temperature signal from each of the reference sensor and the sample sensor to provide a differential temperature between the reference sensor and the sample sensor. In additional examples, the method may further comprise providing differential power to only the sample sensor, based on the generated second control signal, to heat or cool the temperature of the sample sensor to substantially the same temperature as the reference sensor.

In certain embodiments, the method may include configuring the first controller to be a proportional-integral-derivative controller. In other embodiments, the method may include configuring the second controller to be an analog proportional controller. In additional examples, the method may include heating the sample sensor and the reference sensor at a heating rate of 10 Kelvin/second or more.

In another aspect, a method of facilitating calorimeter control, the method comprising providing a control module comprising a first controller configured to receive a temperature signal from only a reference sensor and to generate a first control signal, based on the received temperature signal, to provide average power to a sample sensor and to the reference sensor is provided. In certain examples, the control module can also include a second controller configured to receive temperature signals from both the sample sensor and the reference sensor and to generate a second control signal, based on the temperature signals received from both the sample sensor and the reference sensor, to provide differential power to only the sample sensor.

Additional features, aspects, examples and embodiments are described in more detail below.

BRIEF DESCRIPTION OF THE FIGURES

Certain embodiments are described below with reference to the accompanying figures in which:

FIG. 3 is a schematic of a control system suitable for use with high heating rates, in accordance with certain examples;

FIGS. 4A-4D are photographs of a thin film sensor (XI-296, Xensor Integration, The Netherlands [1]), in accordance with certain examples;

DETAILED DESCRIPTION

Figure 1:
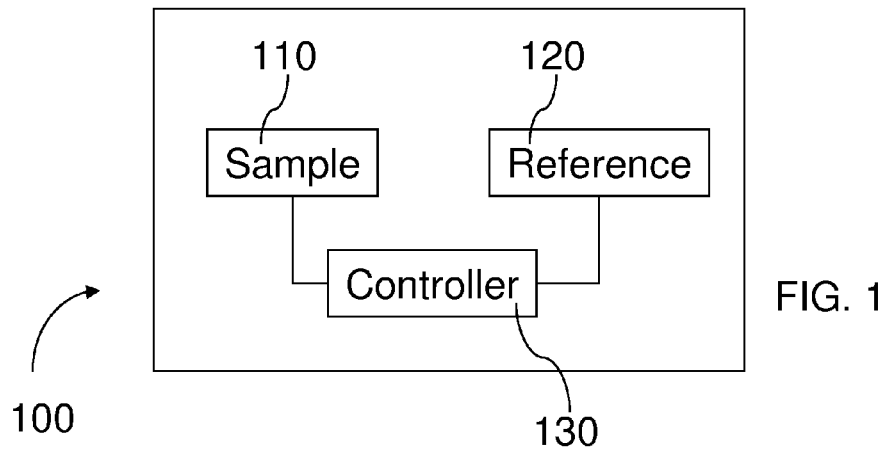
FIG. 1 is a block diagram of a calorimeter, in accordance with certain examples.

Certain embodiments disclosed herein are directed to a calorimeter that is configured to scan at high heating and cooling rates to measure fast occurring chemical and physical processes that occur, for example, on a timescale too quick for measurement using conventional calorimetric devices. For example, certain examples of the devices disclosed herein may be used to characterize polymers, fibers, films, thermosets, elastomers, composites, pharmaceuticals, foods, cosmetics, as well as organic and inorganic materials that undergo chemical and/or physical processes on a fast time scale. The devices may be used to determine various properties including, but not limited to, glass transition temperature ($T_g$), melting temperature ($T_m$), crystallization times and temperatures, heats of melting and crystallization, percent crystallinities, oxidative stabilities, compositional analysis, heat capacities, heats of cure, completeness of cure, percent cure, purities, thermal stabilities, polymorphism, heat set temperatures of recyclates or regrinds. These and other materials and processes may be analyzed using the devices and methods disclosed herein. The response time of certain embodiments of the control systems and devices disclosed herein may be five milliseconds or less, depending on the materials being analyzed and the exact configuration of the device.

In certain embodiments, a calorimeter configured for differential scanning calorimetry (DSC) is provided. In DSC, a sample and a reference are used. The difference in the amount of heat required to increase the temperature of the sample and the reference are measured as a function of heat input (temperature). The sample and the reference are maintained at substantially the same temperature during the analysis. A temperature program may be implemented such that the sample holder temperature is increased as a function of time. The reference is selected so that it has a well-defined or known heat capacity over the desired temperature range.

Unlike existing calorimeters, certain examples of the calorimeters disclosed herein implement an analog power compensation technique. Illustrative devices implementing such power compensation, optionally along with control and data treatment algorithms and measurements, are described in more detail below.

In a particular type of DSC, power compensation may be used. Power compensation is used to maintain the sample and reference at substantially the same temperature. During operation, power may be provided (or removed) to either the sample or the reference depending on the exact process the sample undergoes. For example, where the sample undergoes an endothermic process, power provided to the reference may be decreased to keep the reference at substantially the same temperature as the sample. Alternatively, the power provided to the sample may be increased. Where the sample undergoes an exothermic process, power provided to the reference may be increased to keep the reference at substantially the same temperature as the sample. Alternatively, power provided to the sample may be reduced to keep the sample and the reference at substantially the same temperature.

In certain systems, conventional DSC systems may not provide sufficient accuracy to study chemical and physical changes occurring on the millisecond or less time scale. For example, in polymers, pharmaceuticals, (amorphous) metal alloys metastability is the rule rather than the exception, and the study of the kinetics of such systems has become an important issue. For a thorough understanding of the kinetics of various temperature- and time-dependent processes related to metastability there is an urgent need for new techniques. There is likewise a great need for equipment enabling the use of high heating rates. In addition, it is important to be able to mimic realistic conditions as occurring during a product's life including processing at high cooling rates.

In certain embodiments, a block diagram of a power compensated DSC is shown in FIG. 1. The device 100 includes a sample holder 110 and a reference holder 120. Each of the sample holder 110 and the reference holder 120 includes each own heating element (not shown). When an exothermic (heat yielded) or endothermic (heat absorbed) change occurs in the sample, power or energy is applied to or removed from one or both of the sample and the reference to compensate for the energy change occurring in the sample. A controller 130 is used to determine whether power should be supplied or removed and to which component such power should be supplied or removed. In effect, this power compensation maintains a "thermal null" state at all times. The amount of power required to maintain the system in equilibrium conditions is directly proportional to the energy changes occurring in the sample.

Figure 2:
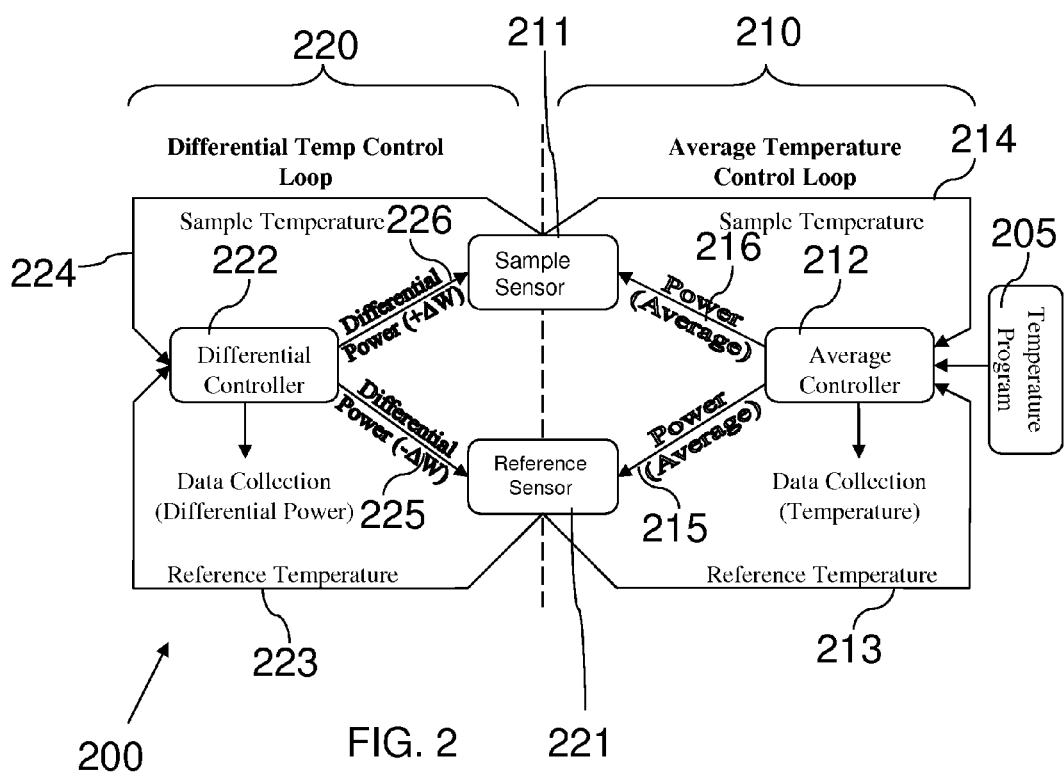
FIG. 2 is a schematic of a conventional control system used in a power compensated differential scanning calorimeter.

A typically control system 200 for a DSC is shown in FIG. 2 The control system includes two separate control loops: a first control loop 210 configured to control the average temperature of the standard and reference holders, and a second control loop 220 configured to control the temperature difference between the sample and reference holders. The average control loop 210 compares the arithmetic average of sample and reference temperatures with a temperature program 205. Average power is defined by difference between reference sensor and programmed temperature. The average control loop 210 includes a controller 212 which is electrically coupled to the sample sensor 211 and the reference sensor 221 through interconnects or electrical connections 214 and 216, respectively. The controller 212 is also electrically coupled to the reference sensor 221 through electrical connections 213 and 215. In some examples, the controller 212 may be configured to provide power, or send a signal to another device to provide power, to the heaters of both the sample 211 and reference 221 sensors through electrical connections shown as 216 and 215, respectively. While shown as having separate connections in FIG. 2 for providing power and sensing the temperature, the controller may have a single electrical connection to the sample holder 211 and a single electrical connection to the reference holder 221. If there is a deviation in temperature between the sample 211 and reference 221 holders, then the average control loop is configured to provide the same electrical output to both the sample holder 211 and the reference holder 221. Due to the feedback, the difference between measured average temperature and programmed temperature is minimized. If the temperature desired in the temperature program is greater than the average temperature of the sample holder 211 and the reference holder 221, more power will be provided to each of the heaters, which, like the thermometers, are embedded in the sample holder 211 and reference holder 221 to provide a short response time for the system.

The differential temperature control loop 220 of the DSC shown in FIG. 2 is configured to measure the temperature difference between both the sample holder 211 and the reference holder 221. The differential temperature control loop 220 includes a controller 222 electrically coupled to the sample holder 211 and the reference holder 221 through interconnects 224 and 223, respectively. The controller 222 may also be coupled to the sample holder 211 and the reference holder 221 through connection 226 and 225, respectively, to adjust the differential power increments provided to the sample holder 211 and the reference holder 221. For example, signals representing the sample and reference temperatures, measured, for example, by platinum thermometers of the holders, are provided to the differential temperature amplifier. The differential temperature amplifier output will then adjust the differential power increment provided to the reference and sample heaters in the direction and magnitude necessary to correct any temperature difference between them. In the case of a lower temperature of the sample holder, for example, due to an endothermic transition, additional power may be provided to the sample holder. In order to minimize the difference most effectively and to keep a strict symmetry of the measuring system, the same amount of power may be subtracted on the reference side. This power is recorded and together with the average temperature profile it provides the complete information about the heat flow to the sample. This scheme is implemented, for example, in PerkinElmer DSC calorimeters working up to 8 K/s scanning rate with milligram samples. This control allows for a relatively simple determination of the differential heat flow from the remaining temperature differences between sample and reference cups. In the PerkinElmer differential power compensation DSC, the additional heat needed (or released) during an endothermic (exothermic) event in the sample is finally provided by the average controller because the differential controller does not add or remove heat from the system due to its symmetric operation. In this configuration, the controllers of both control loops must react fast enough to avoid deviations from the programmed temperature. Therefore, it is common practice to use proportional controllers for both controllers of the first control loop 210 and the second control loop 220.

In certain embodiments disclosed herein, the control loop (and more particularly, the average controller 212) shown in FIG. 2 may not respond precisely enough at high heating rates such as, for example, those exceeding 10 K/second to provide adequate measurements. For example, if higher heating rates and sensitivity are desired, the average signal, if generated using the control system of FIG. 2, may contain small and fast events from the nanogram quantities of sample which will not be detected using the conventional control system shown in FIG. 2. To overcome such problems, a control system as shown in FIG. 3 may be used. Similar to the control system of FIG. 2, the control system 300 comprises two control loops 310 and 320 but the configuration and/or function of each of the control loop differs from those shown in FIG. 2. It may be beneficial to separate average and difference control to avoid any cross talk between both control loops 310 and 320. For example, the control reference temperature may be measured without measuring an average temperature of the sample holder. Thus, the sample temperature lead 312 of the first control loop 310 may be omitted, as shown schematically using an "X" in FIG. 3, and reference controller 311 does not measure the average temperature of the sample holder 316. In the average temperature control loop 310, the controller 311 may be electrically coupled only to the reference holder 316 through lead 313 without any direct electrical connection for monitoring the temperature of the sample holder 326. This configuration permits the use of a relatively slow but precise PID controller for the reference temperature control. For example, time resolution for the control of the reference temperature may be orders of magnitude slower compared to the differential controller 321. In addition, output power range (dynamics) of the reference controller 311 is orders of magnitude larger than for the differential controller 321. For example, the differential temperature control loop 320 may have a time constant of about 3 ms, whereas the average temperature control loop 310 has a time constant of about 20 ms. The integral part of the reference controller 311 assures that the difference between program temperature and reference temperature is practically zero. Assuming high symmetry between the reference and sample sensors, the same temperature profile in the sample sensor as in the reference sensor may unexpectedly be achieved by applying substantially the same output voltage of the reference controller 311 to the heaters of the sample sensor 326 and the reference sensor 316 through, for example, connections 314 and 315.

In the second control loop 320, which is the differential control loop, the controller 321 is electrically coupled to the sample sensor 326 and the reference sensor 316, through connections 322 and 323, respectively, and is configured to detect any differences between reference and sample sensor temperatures. The controller 321 can then add or subtract its output voltage solely on (or from) the sample sensor 326. That is, the differential power to the reference holder 316 is not monitored, detected, used or altered using controller 321, as shown in the "X" for the differential power connection to the reference holder 316. Using this configuration to provide a total separation between both of controller 311 and 321, the unexpected results of high heating rates along with high accuracy can be achieved. In addition, this configuration permits the use of a precise (but slow) PID controller for control of the reference temperature and a highly sensitive and fast proportional controller for the differential controller.

In certain examples, the control system shown in FIG. 3 may be used to monitor chemical and physical processes of samples using a heating rate (or cooling rate) of 1 K/second or more, more particularly about 10 K/second or more, for example about 1-10,000 K/second, more particularly 10-1000 K/second, e.g., 10-500 K/second, 10-100 K/second or any value within these illustrative ranges. Such high heating rates and the calorimeters described herein permit the study of chemical and physical transitions that occur on time scales too rapid for study using conventional calorimeters. In some examples, the heating may be linear such that a linear increase between a starting temperature and a final temperature is implemented with the heating rate being the slope of temperature as a function of time. Similarly, once the final temperature is reached, a cooling rate, which may be the same or similar to the heating rate, may be used to study processes during cooling of the sample and reference holders. In other examples, the heating and/or cooling may be stepped, non-linear or may take other forms depending in the material being studied and the desired information therefrom.

In certain embodiments, the control system described herein may be used with conventional calorimetric crucibles or with thin film sample holders, depending on the desired heating rates (or cooling rates). For example, high heating rates may be limited by the mass of the measuring cell. By using thin films, such as those described by Hager, Allen and co-workers and Lopeandia et al., along with the control systems disclosed herein, small amounts of sample may be studied using high heating and cooling rates. In addition, the gap in scanning rate between DSC and fast scanning calorimetric techniques ranging between 8 . . . $10^2$ K/s, an area of interest due to many material processing steps being within this cooling rate range, may be bridged. Illustrative thin film sensors include, but are not limited to, those including XI-296, XI-270, XI-272 and XI-292 commercially available from Xensor Integration, The Netherlands and other sensors including, for example, those described in the van Herwaarden, A. W. article listed herein.

In certain embodiments of the thin film sensors, the sizes and dimension of the films may be selected such that they have a low heat capacity as compared to traditional crucibles or cups used in calorimetry. For examples, instead of using cups with a mass of about 1 gram, the devices disclosed herein may include two high sensitive, low addenda heat capacity thin film sensors, e.g., a XI-296 sensor such as those used for single-sensor fast scanning calorimeters. In certain embodiments, the measuring cell may include a silicon frame having dimensions of about 2.5×5 $mm^2$ fixed on a standard integrated circuit housing, e.g. a TO-5 housing. Calorimeters including the thin films may also include a heater and a thermopile embedded at the center of a freestanding SiN membrane (e.g., 0.5 µm thick) as shown, for example, in FIGS. 4A-4D. FIG. 4A shows the chip (dark) mounted on a TO-5 housing. In FIG. 4B, the thick chip with a silicon frame (dark) and the free standing SiN membrane (light area in the center of the chip) is shown. A more detailed view on the chip is presented in FIG. 4C where the wiring to the measurement area in the center is seen. The arrangement of the heater (thick stripes) and the thermopiles (thin stripes) in the center of the membrane is shown on FIG. 4D. The size of the heated area may vary from about 8 microns to about 100 microns, for example, about 8 microns by 10 microns or about 60 microns by 80 microns. A desired number of thermopiles may be placed in the heated area to allow fast and precise temperature measurement. The thermopiles may be produced using suitable lithographic techniques and p- and n-doped silicon, and the hot junctions are placed just in between the two heater stripes while the cold junctions are placed on top of the silicon frame (FIG. 4C, left and right of the free standing membrane). The thermopiles typically include a series of thermocouples that can measure temperature of and/or provide/take away heat to or near the thin films. The exact type of thermopile used may vary and illustrative types of thermopiles include, but are not limited to, semiconducting thermopiles, and thermopiles including one or more of known types of thermocouples. For example, illustrative thermocouple types include, but are not limited to, Type B (Platinum/30% Rhodium (+) versus Platiumt/6% Rhodium (−)), Type E (Nickel/10% Chromium (+) versus constantan (−)), Type J (Iron (+) versus constantan (−)), Type K (Nickel/10% Chromium (+) versus Nickel/5% Aluminum-Silicon (−)), Type R (Platinum/13% Rhodium (+) versus Platinum (−), and Type S (Platinum/10% Rhodium (+) versus Platinum (−)), as described, for example, in ANSI C96.1-1964. Additional thermocouples such as, for example, pure platinum, platinum palladium, platinum iridium, platinum tungsten and tungsten rhenium thermocouples, however, will be selected by the person of ordinary skill in the art, given the benefit of this disclosure. As detailed herein, many different types of suitable thin films sensors are commercially available from numerous suppliers.

In some examples, the thin film may be configured with five or six semiconducting thermopiles placed inside the heating area with the "hot" junction in the center, and the "cold" junction on the frame of the sensor (see FIGS. 4C and 4D). For fast scanning experiments, such as those where a heating rate of about 10 K/second or more is used, the sample may be placed on the top of the thin film area that is heated so that reliable information about sample temperature for thin samples can be obtained. Otherwise the strong temperature gradients outside the heated area may adversely affect the measurements.

In certain embodiments that implement thin film sensors, one or more suitable algorithms may be used to determine the amount of heat produced or lost. For example, separation of the control loops in the devices disclosed herein makes the calculation of sample heat capacity more difficult in comparison to the symmetric power compensation scheme such as those commonly used in power compensation DSC, but allows going to higher heating rates with reliable average temperature control. In general, the thermal contact between the heater and a thin sample is sufficiently good because of adhesive forces and any residual heat loss may be neglected. The heat capacities and thermal resistances of the thin film-heater and of the thermopile are also negligibly small. The main heat capacity of the cell is the effective heat capacity of the heated part of the membrane, which is about $2\times10^{-7}$ J/K at room temperature. The system can be described by the following parameters: the effective heat capacity of the central part of the cell $C_0$, the heat capacity of the sample C, and the coefficient of heat exchange, $\xi$, between the central part of the cell and the environment. The resistive film-heater, about. 1 kOhm resistance, provides the heat flow $P_0(t)$, which is supplied to the thin film/sample interface and propagates through the sample, membrane and the ambient gas. Using these variables, the equation of the heat balance may be represented as:

$$(C + C_0)\frac{dT}{dt} = P_0 - \xi(T(t) - T_0) \qquad (1)$$

where T(t) and $T_0$ are the temperatures of the heating region and of the environment, respectively, $P_0$ is the power provided to the system, and C and $C_0$ are the heat capacity of the sample and the thin film sensor, respectively. Assuming a perfectly symmetric differential system (both sensors are always at substantially the same temperature), the heat losses to the surrounding (the second term on the right side of the equation), and the addenda heat capacities $C_0$ of both sides are compensated. Then the difference of equation 1 for sample and reference sensors provides the following equation.

$$C\frac{dT}{dt} = P_{difference}. \quad (2)$$

Where $P_{difference}$ is the difference between the power supplied to the sample and the reference sensors. $P_{difference}$ can be obtained from the remaining temperature difference between both sensors and the other quantities measured, see, for example, FIG. 7B, using the calorimeters disclosed herein.

In certain embodiments, the calorimeters disclosed herein may be conjugated or hyphenated to other analytical devices such that measurements other than heat measurements may also be performed on a sample. In some examples, one or more other analytical devices may be conjugated to the calorimeter for additional analysis of the materials being analyzed or for analysis of gases evolved during the calorimetric analysis. Illustrative analytical devices include, but are not limited to, a mass spectrometer (MS), an infrared (IR) spectrometer, a gas chromatograph (GC) and combinations of these techniques. Block diagrams illustrating some hyphenated devices are shown in FIGS. 5A-5D. Such hyphenated devices may be particular useful for evolved gas analysis, where one or more gases is evolved from the sample during a calorimetric measurement. Such gases may be directed or drawn into another instrument or device using suitable devices such as, for example, vacuum pumps, fans, head space sampling and the like. In some examples, a heated tube may provide fluid coupling between the calorimeter and the MS such that species that evolve as gases in the thermal analysis device may be kept as gases during the transfer to the MS. Additional suitable devices and methods for transferring species from a thermal analysis device to a MS will be readily selected by the person of ordinary skill in the art, given the benefit of this disclosure.

Figure 5A:
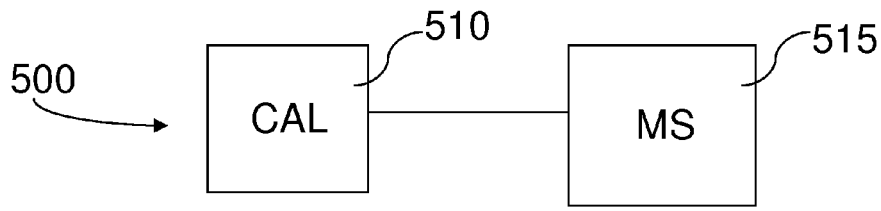
FIGS. 5A-5D are block diagrams of hyphenated devices, in accordance with certain examples.

Referring to FIG. 5A, a system 500 may comprise a calorimeter 510, shown as CAL in the figures, coupled to a mass spectrometer 515. The calorimeter 510 may be configured as described herein, for example, with separate control loops. The mass spectrometer 515 may be any mass spectrometer commonly used in chemical analysis such as those commercially available, for example, from PerkinElmer Life and Analytical Sciences, Inc. (Waltham, Mass.). Illustrative mass spectrometers include, but are not limited to, those configured to use or implement a magnetic sector mass analyzer, a quadrupole mass analyzer, an ion trap analyzer, a time-of-flight analyzer, those implementing electrospray deionization and other suitable mass analyzers that may separate species with different mass-to-charge ratios. It may be desirable to include one or more valves, fittings or devices to compensate for the difference in pressure between the calorimeter 510 and the mass spectrometer 515. Such pressure compensation will be achieved by the person of ordinary skill in the art, given the benefit of this disclosure.

Figure 5B:
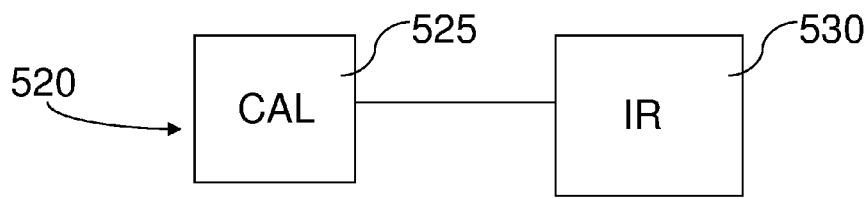

Referring to FIG. 5B, a system 520 may comprise a calorimeter 525 coupled to an infrared (IR) spectrometer 530. The calorimeter 525 may be configured as described herein, for example, with separate control loops. The infrared spectrometer may be any commonly used infrared spectrometers, such as, for example, a continuous wave infrared spectrometer, a single or a dual beam infrared spectrometer, or an interference spectrometer such as a Fourier transform infrared spectrometer. Suitable other infrared spectrometers and suitable methods for coupling a calorimeter to an IR device will be recognized by the person of ordinary skill in the art, given the benefit of this disclosure.

Figure 5C:
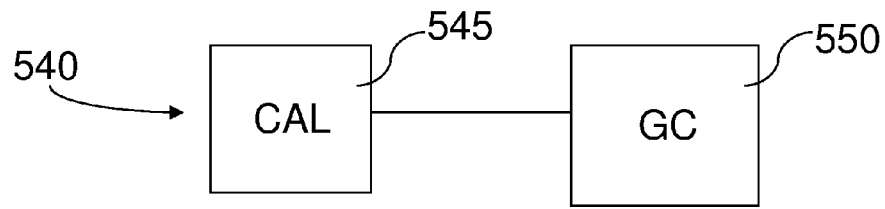

Referring to FIG. 5C, a system 540 may comprise a calorimeter 545 coupled to a gas chromatography system (GC) 550. The calorimeter 545 may be configured as described herein, for example, with separate control loops. The GC 550 may receive evolved gas from the calorimeter 545 and separate species within the evolved gas. For example, it may be desirable to separate gaseous reaction products evolved during the calorimetric analysis. It will be within the ability of the person of ordinary skill in the art, given the benefit of this disclosure, to select suitable GC devices for use with the calorimeters disclosed herein.

Figure 5D:
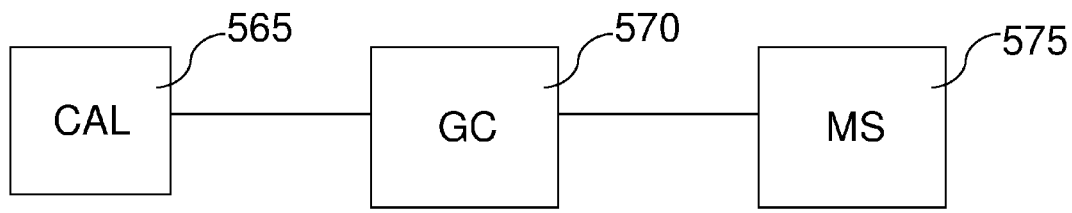

Referring to FIG. 5D, a system 560 may comprise a calorimeter 565 coupled to a gas chromatograph 570 which itself is coupled to a mass spectrometer 575. The calorimeter 565 may be configured as described herein, for example, with separate control loops. The GC 570 and the MS 575 may each be, for example, any of the illustrative GC and MS devices discussed in reference to FIGS. 5A and 5C or other suitable GC and MS devices. The illustrative systems shown in FIGS. 5A-5D may also include additional components such as, for example, autosamplers, filters, analysis systems and software, computer interfaces and the like.

In accordance with certain examples, the instrument configurations described herein may be controlled or used with, at least in part, a computer system. The computer systems may be, for example, general-purpose computers such as those based on Unix, Intel PENTIUM-type processor, Motorola PowerPC, Sun UltraSPARC, Hewlett-Packard PA-RISC processors, or any other type of processor. It should be appreciated that one or more of any type computer system may be used according to various embodiments of the technology. Further, the system may be located on a single computer or may be distributed among a plurality of computers attached by a communications network. A general-purpose computer system according to one embodiment may be configured to perform any of the described functions including but not limited to: data acquisition, calorimeter control, data analysis and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. The memory is typically used for storing programs and data during operation of the computer system. Components of the computer system may be coupled by an interconnection mechanism, which may include one or more busses (e.g., between components that are integrated within a same machine) and/or a network (e.g., between components that reside on separate discrete machines). The interconnection mechanism enables communications (e.g., data, instructions) to be exchanged between system components. The computer system typically is electrically coupled to an interface on the system such that electrical signals may be provided from the system to the computer system for storage and/or processing.

The computer system may also include one or more input devices, for example, a keyboard, mouse, trackball, microphone, touch screen, analog to digital converter (ADC, DAQ boards), and one or more output devices, for example, a printing device, status or other LEDs, display screen, speaker, digital to analog converter (DAC boards) and the like. In addition, the computer system may contain one or more interfaces that connect the computer system to a communication network (in addition or as an alternative to the interconnection mechanism). The storage system of the computer typically includes a computer readable and writeable nonvolatile recording medium in which signals are stored that define a program to be executed by the processor or information stored on or in the medium to be processed by the program. For example, the heating profiles, heating rates, cooling rates and the like may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in storage system or in memory system. The processor generally manipulates the data within the integrated circuit memory and then copies the data to the medium after processing is completed. A variety of mechanisms are known for managing data movement between the medium and the integrated circuit memory element, and the technology is not limited thereto. The technology is not limited to a particular memory system or storage system.

The computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component.

In some examples, the computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used. In addition or alternative to a processor, the computer system may include a controller such as for example and 8-bit or 16-bit controller. Other controllers such as 32-bit or higher controller may also be used in place of a processor or in addition to the processor of the computer system.

The processor and operating system together define a computer platform for which application programs in high-level programming languages can be written. It should be understood that the technology is not limited to a particular computer system platform, processor, operating system, or network. Also, it should be apparent to those skilled in the art that the present technology is not limited to a specific programming language or computer system. Further, it should be appreciated that other appropriate programming languages and other appropriate computer systems could also be used.

In certain examples, the hardware or software is configured to implement cognitive architecture, neural networks or other suitable implementations. One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. Various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

Various embodiments may be programmed using an object-oriented programming language, such as SmallTalk, Basic, Java, C++, Ada, LabView (National Instruments) or C# (C-Sharp). Other object-oriented programming languages may also be used. Alternatively, functional, scripting, and/or logical programming languages may be used. Various aspects may be implemented in a non-programmed environment (e.g., documents created in HTML, XML or other format that, when viewed in a window of a browser program, render aspects of a graphical-user interface (GUI) or perform other functions). In some examples, the desired heating rates, cooling rates, sampling rates and the like may be selected from one or more pull down menus of the graphical user interface. Various aspects may be implemented as programmed or non-programmed elements, or any combination thereof. In certain examples, a user interface may be provided such that a user may enter desired parameters such as, for example, the heating rates, the cooling rates, sample size, initial power and the like. Other features for inclusion in a user interface will be readily selected by the person of ordinary skill in the art, given the benefit of this disclosure.

Figure 6:
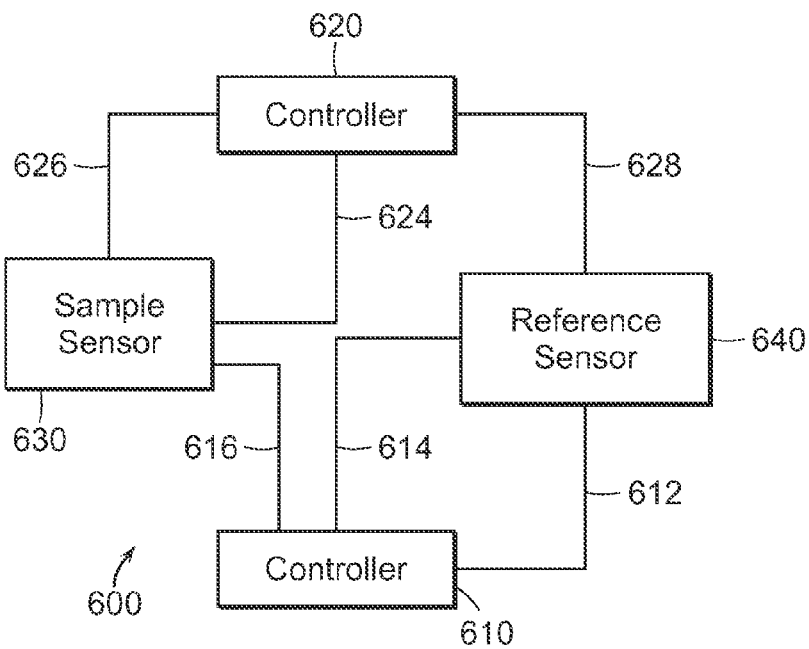
FIG. 6 is a block diagram of a control system suitable for use with high heating rates, in accordance with certain examples.

In certain embodiments, a control system configured to control the temperature of a sample sensor and a reference sensor of a calorimeter is provided. The system is shown in a block diagram in FIG. 6. In certain examples, the control system 600 comprises a first controller 610 and a second controller 620 each electrically coupled to a sample sensor 630 and a reference sensor 640 through at least one electrical connection. The first controller 610 may be configured to receive a temperature signal from the reference sensor 640 through connection 612. The first controller 610 may generate a first control signal based on the temperature signal from the reference sensor 640, e.g., based solely on the temperature signal from the reference sensor 640, and provide power to both the sample sensor 630 and the reference sensor 640 through connections 616 and 614, respectively, based on the generated first control signal. In some examples, the second controller 620 may be configured to receive a temperature signal, from the sample sensor 630 and the reference sensor 640 through connections 626 and 628, respectively. In certain instances, the second controller 620 may generate a second control signal to provide differential power only to the sample sensor 630, based on the generated second control signal, through electrical connection 624. In certain examples, the sample sensor and the reference sensor may each be thin film sensors that can respond rapidly to alter their temperature during high heating rates. The sample sensor and the reference sensor each typically include a sample holder, a heating element (for example, a resistive heating element), and a temperature sensing element (for example, a thermocouple, thermometer or the like). The signals provided to the sample sensor 630, and the reference sensor 640 are suitable signals to increase (or decrease) the heat provided by the heating element of that particular sensor so the sample sensor 620 and the reference sensor 640 may remain at substantially the same temperature during the analysis. In some examples, the first controller 610 may be a PID controller, and the second controller 620 may be a proportional controller or other suitable controller that can detect rapid heat changes that may occur due to high heating rates.

In some examples, the systems disclosed herein may include additional components such as, for example, an autoloader. The autoloader may be configured to load samples (or sensors that include a sample) sequentially into and out of the system such that the system may perform measurements without user intervention or monitoring. The autoloader may comprise, for example, a robotic arm and/or motor that can securely grip the samples/sensors and load them into a desired position in the system. The system may include other electrical components such as operational amplifiers, gain control devices and the like. The system may include a bar code reader so that each sample may be encoded with a bar code and the measurements of each sample can be associated with its respective bar code. Additional components and features for including in the devices and systems disclosed herein will be readily selected by the person of ordinary skill in the art, given the benefit of this disclosure. In some examples, the autoloader may be configured to load only sample, whereas in other examples, the autoloader may load sensor plus sample into the sampling space.

In certain examples, a method of measuring physical or chemical changes using a calorimeter is disclosed. In certain examples, the method comprises controlling a sample sensor and a reference sensor by generating a first control signal using a first controller, the first control signal based on receipt of a temperature signal from only the reference sensor of the calorimeter by the first controller. In some examples, the method may also comprise providing power to the reference sensor and the sample sensor, based the generated first control signal, to control the average temperature of the reference sensor and the sample sensor, e.g., without sensing the temperature of the sample sensor. In other examples, the method may also comprise generating a second control signal using a second controller, the second control signal based of receipt of a temperature signal from each of the reference sensor and the sample sensor to provide a differential temperature between the reference sensor and the sample sensor. In certain embodiments, the method may further comprise providing power to only the sample sensor, based on the generated second control signal, to heat or cool the temperature of the sample sensor to substantially the same temperature as the reference sensor. In certain examples, the method may include configuring the first controller to be a proportional-integral-derivative controller. In other examples, the method may include configuring the second controller to be an analog proportional controller. In certain embodiments, the method may include heating the sample sensor and the reference sensor at a heating rate of 10 Kelvin/second or more, e.g., 20, 30, 40, 50, 60, 70, 80, 90, or 100 Kelvin/second or more.

In certain embodiments, a method of facilitating calorimeter control is provided. Such method may be performed by providing the controller (or control loop) configurations described herein in the form of a control module, for example. In certain examples, the method comprises providing a control module comprising a first controller configured to receive a temperature signal from only a reference sensor and to generate a first control signal, based on the received temperature signal, to provide average power to a sample sensor and to the reference sensor and a second controller configured to receive temperature signals from both the sample sensor and the reference sensor and to generate a second control signal, based on the temperature signals received from both the sample sensor and the reference sensor, to provide differential power to only the sample sensor. The module can interface with existing calorimetric devices or may itself include spaces for a sample sensor and a reference sensor that can be coupled to the controller of the module as described herein.

Certain specific examples are described in more detail below to facilitate a better understanding of the technology disclosed herein.

EXAMPLE 1

Calorimeter Construction

Figure 7A:
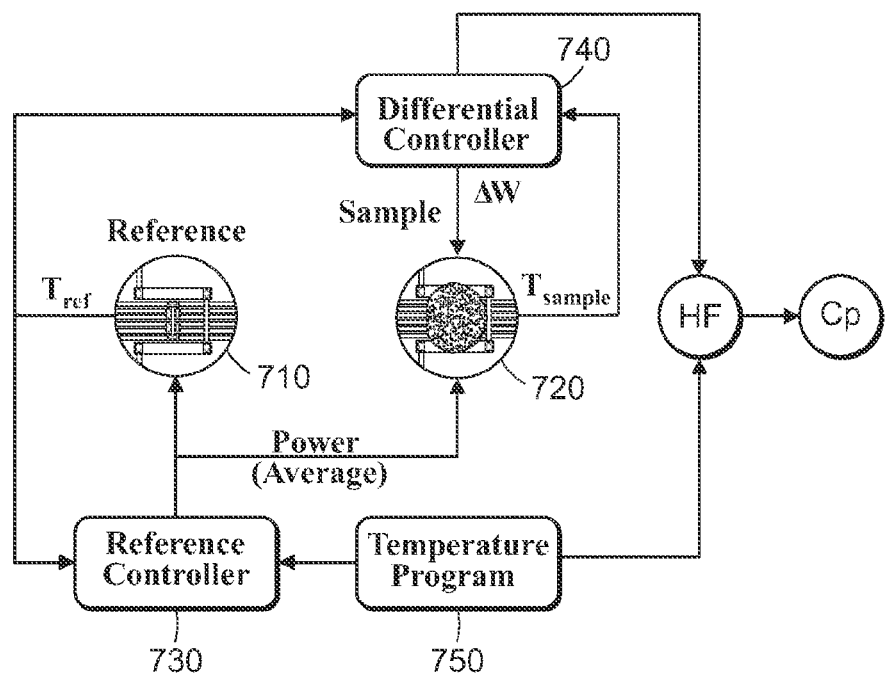
FIGS. 7A and 7B are schematic of a calorimeter assembled for testing metals and polymers and FIG. 7C is a photograph of a thermostat including two sensors, in accordance with certain examples.
Figure 7B:
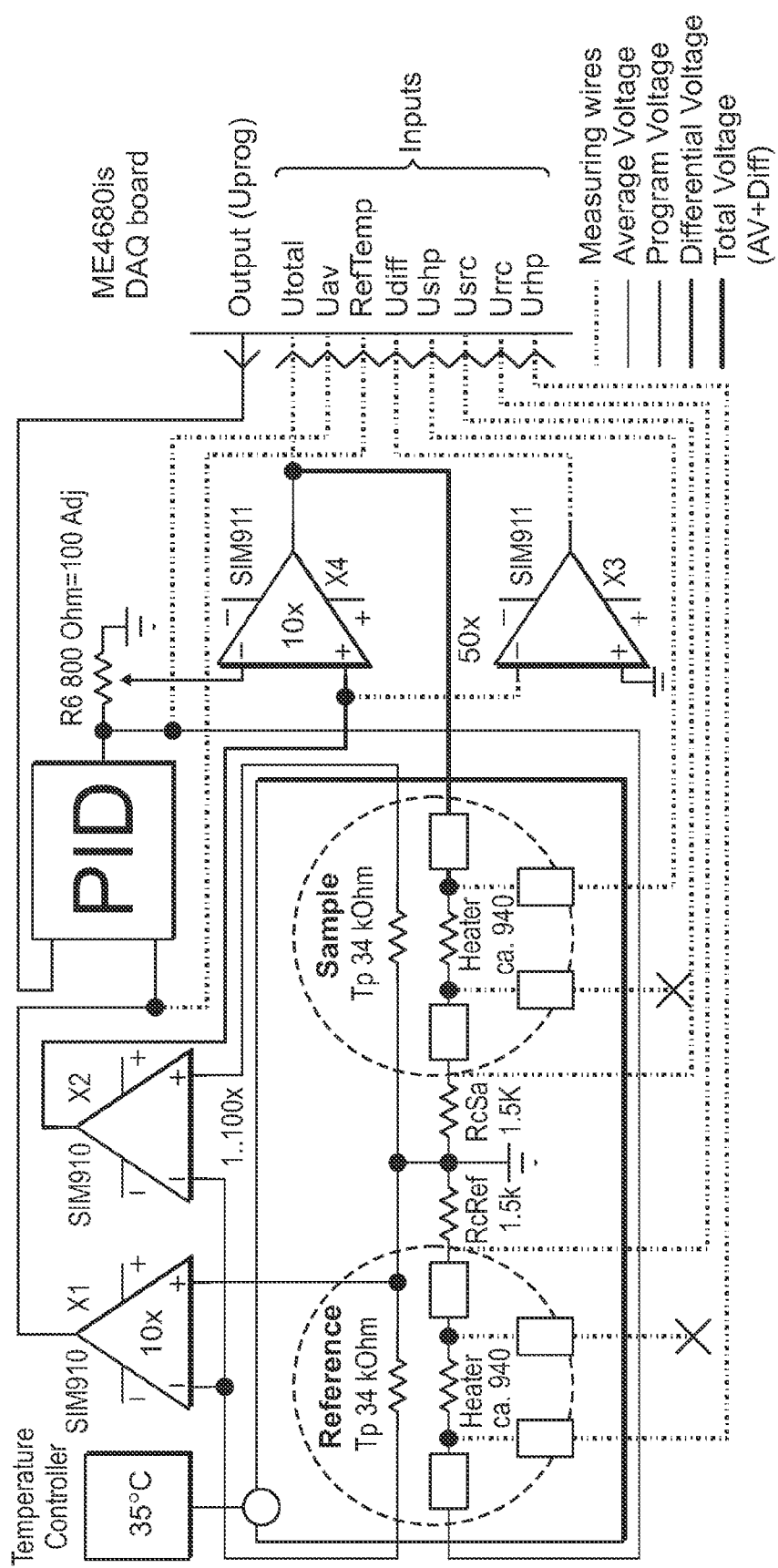
Figure 7C:
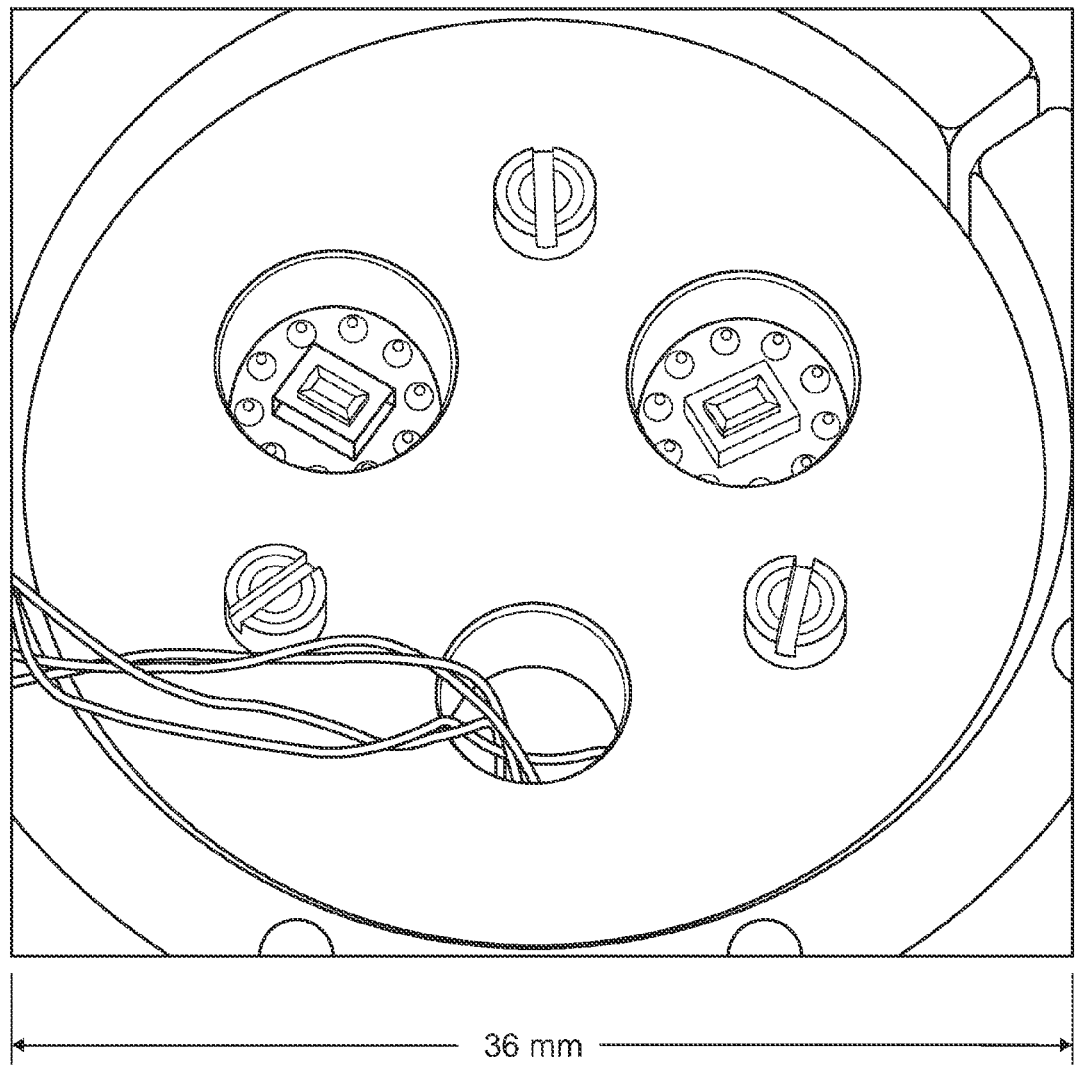

A calorimeter having a control system with two control loops was constructed as follows: two calorimetric sensors, one with sample the other without sample, were placed in a thermostat, as shown in the photograph of FIG. 7C, at a controlled temperature, e.g. 35° C. as indicated in FIG. 7B, and with a selected ambient gas, e.g. helium or nitrogen at 50 kPa or 100 kPa. The sensor was in good thermal contact to the thermostat and the cold junction temperature of the thermopile equaled the thermostat temperature. The sensors were connected to the two control loops as schematically shown in FIG. 7A and in detail in FIG. 7B. Amplifier X1 (SIM910, low output noise, 1 MHz bandwidth voltage amplifier) amplified the thermopile output from the reference sensor 710 and provided it to the PID controller 730 (SIM960, analog PID) which serves as the reference controller for the average temperature control loop 310, as described in reference to FIG. 3. The PID compares the measured reference sensors' temperature with the predefined temperature program 750. The output of the PID was provided to the heater of the reference sensor 710, which was in series with some wire resistors indicated by boxes in FIG. 7B and a constant resistor of 1.5 KOhm allowed measurement of the current through the heater. All voltages needed to recalculate power and finally differential power as needed in Eq. (2) were measured by a DAQ board ME4680 is from Meilhaus Electronic. The board also provided the temperature program (Uprog). Voltage across the heater as well as the constant resistor was measured in four (three) wire connections to compensate for wire resistors. Amplifier X2 (SIM910) amplified the temperature difference signal coming from the thermopiles of the reference 710 and the sample sensor 720, which were connected in series. Amplifier X4 (SIM911) was used to add the output from X2 to the output of the PID. X2 and X4 acted as the differential controller described in reference to FIG. 3. The output of X4 was provided to the heater of the sample sensor 720. Again voltage and current to recalculate power and differential power was measured using the configuration shown in FIG. 7B. Input range of X4 was limited to 1 Volt. Therefore the output of the PID (0-10 V) was divided by 10 using resistor R6 so not to overload X4. Adjusting R6 further allowed compensating small differences between the two sensors. X3 (SIM911) amplified the temperature difference signal further and was used for the calculation of the differential power. All amplifiers and the PID were produced by Stanford Research Systems, Inc., and were placed in a Small Instrumentation Modules SIM900—Mainframe, also from Stanford Research Systems, Inc. The latter allowed full control of all functions from the computer via a GPIB interface.

In operation of the device shown in FIGS. 7A and 7B, analog devices were used to shorten response time and therefore allow high rate temperature processing. As described above, an analog PID controller was used to control reference sensor temperature and to provide average power to both sensors. The programmed temperature as function of time was supplied to the PID from a computer or controller according to a user-defined temperature profile. As soon as the temperature (thermopile voltage) of the sample side sensor was different from reference sensor temperature, the difference was amplified and added to the voltage that was provided to the sample side heater. The differential control loop consisted of a high frequency analog amplifier so that it had a very fast response time on the order of one or a few microseconds. Differential power and all voltages needed for measurements were collected by the computer using, for example, an ADC/DAC board. The used SRS Small Instrumentation Module analog device frame permitted controlling parameters of the analyses from a computer. The program for managing the experiment and obtaining data was developed using LabView™.

EXAMPLE 2

Metal Testing

For testing the device described in Example 1, melting and crystallization of small (micron diameter) spherical metal particles was studied. For such first order transitions the heat capacity and the resulting heat flow curves are known. Even though the particles were small, the heat of fusion was large compared to the addenda heat capacity of the sensors. Therefore, strong deviations of the programmed temperature profile were detected at low differential gain settings, as described below. The instrument was capable of detecting such transitions and providing differential power to control the calorimeter.

Figure 8A:
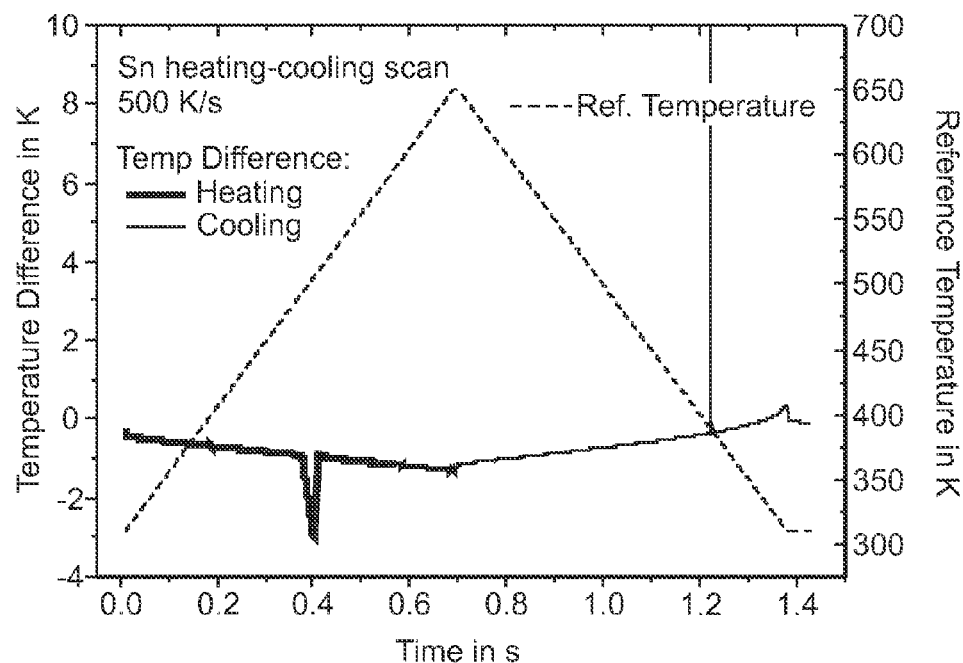
FIGS. 8A and 8B show the results of testing metal particles, in accordance with certain examples.
Figure 8B:
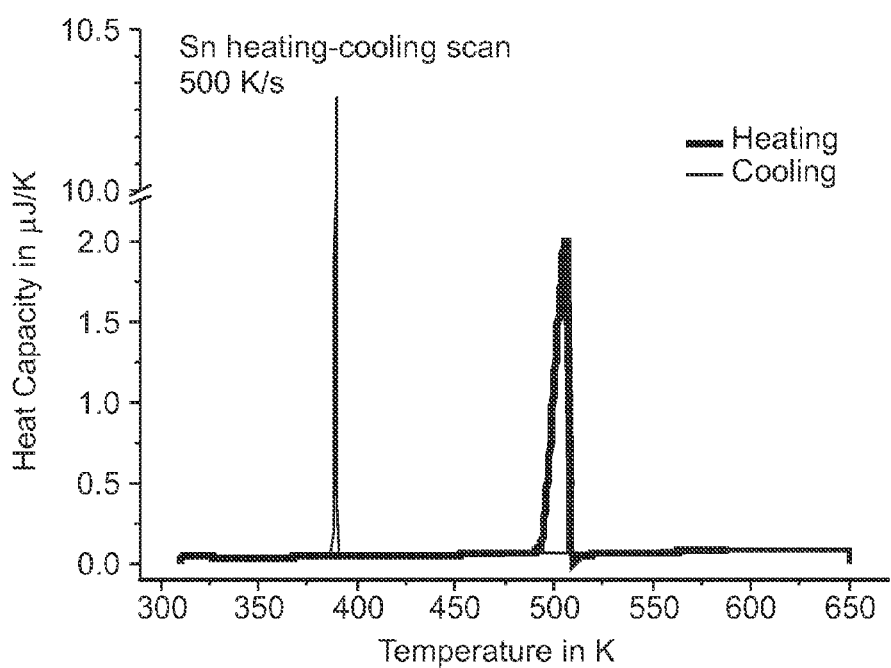

The results of heating single spherical tin particles (about 350 nanograms) with a heating-cooling rate of 500 K/s measured with the device of Example 1 are shown in FIGS. 8A and 8B, with the reference sensor being an empty sensor in all the measurements described below. FIG. 8A shows the temperature program and remaining temperature difference between sample and reference sensors. FIG. 8B shows the heat capacity from the data shown in FIG. 8A. On heating, the peak shape is determined by the heat transfer from the sensor to the relatively heavy sample. The well known linear leading edge of the peak is shown in FIG. 8A. From the width of the peak the time for melting (the heat transfer) was estimated as 29 milliseconds. Crystallization on cooling was much faster because of about 100 K supercooling. The crystallization can be considered nearly as a delta function. The response time of the instrument was estimated to be 3 milliseconds. The crystallization peak nicely demonstrated the power of the device in handling fast processes.

Figure 9A:
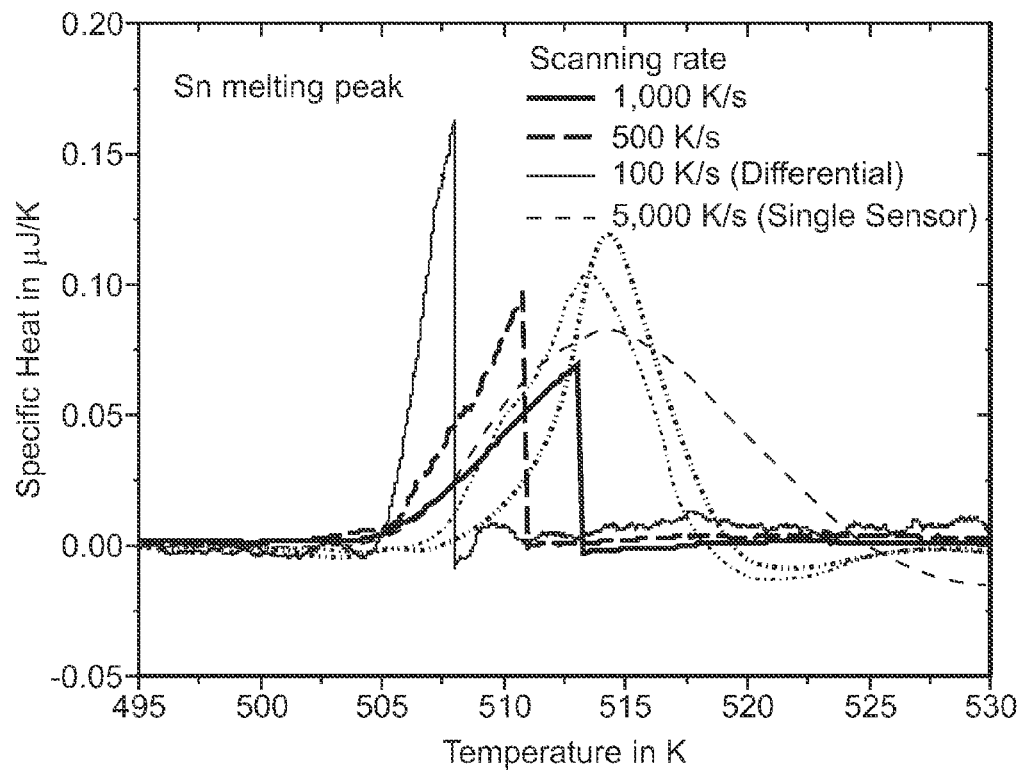
FIGS. 9A and 9B shows the results of melting metal particles at different heating rates, in accordance with certain examples.
Figure 9B:
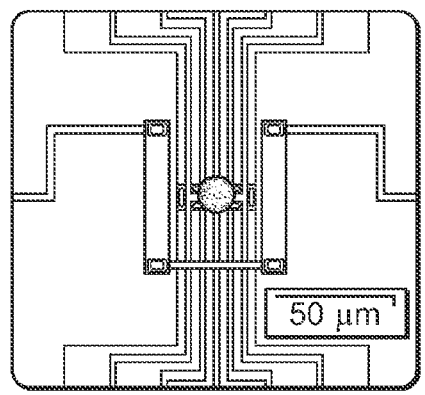

Referring to FIG. 9A, the results of heating single spherical tin particles (about 35 nanograms) using a single sensor device, as described in the Minakov (Rev. Sci. Instr. 2007) article listed below, and the device of Example 1 are shown. In FIG. 9A, the melting curves for the small tin sample were compared for the single sensor chip calorimeter without active control and the power-compensated differential chip calorimeter at different heating rates. While the single sensor device yielded very round curves, the differential device of Example 1 provided the expected triangle like melting curves as known from power compensation DSCs. The differential setup provided more realistic data with less distortion by the instrument. FIG. 9B shows placement of the sample on the sensor.

Figure 10A:
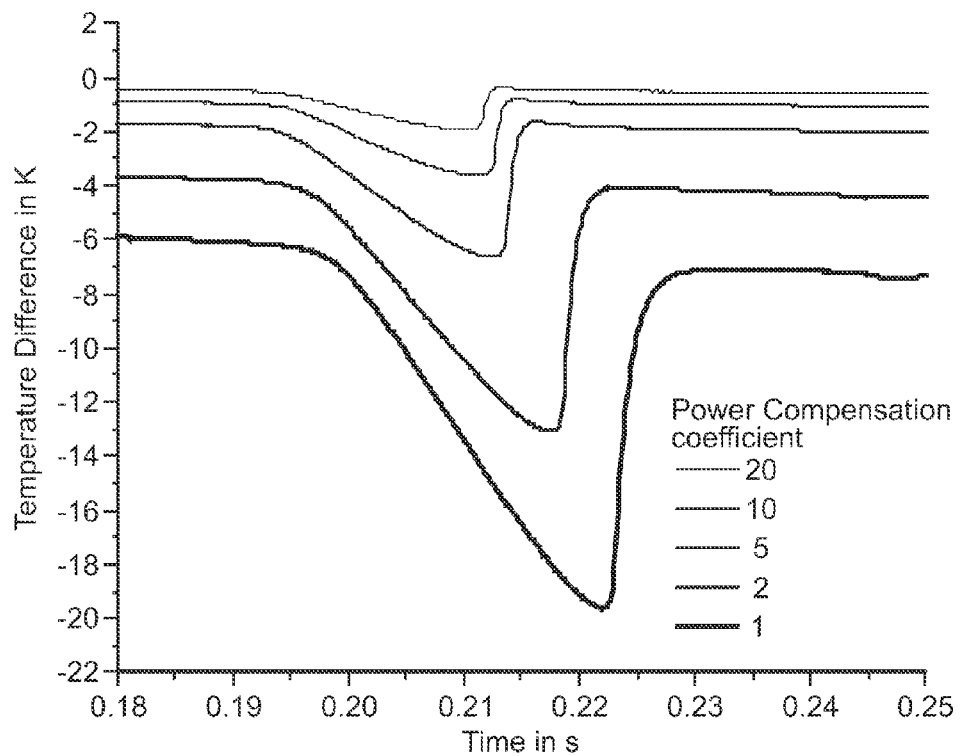
FIGS. 10A and 10B show the temperature differences of the sample and reference sensors at different gain settings, in accordance with certain examples.
Figure 10B:
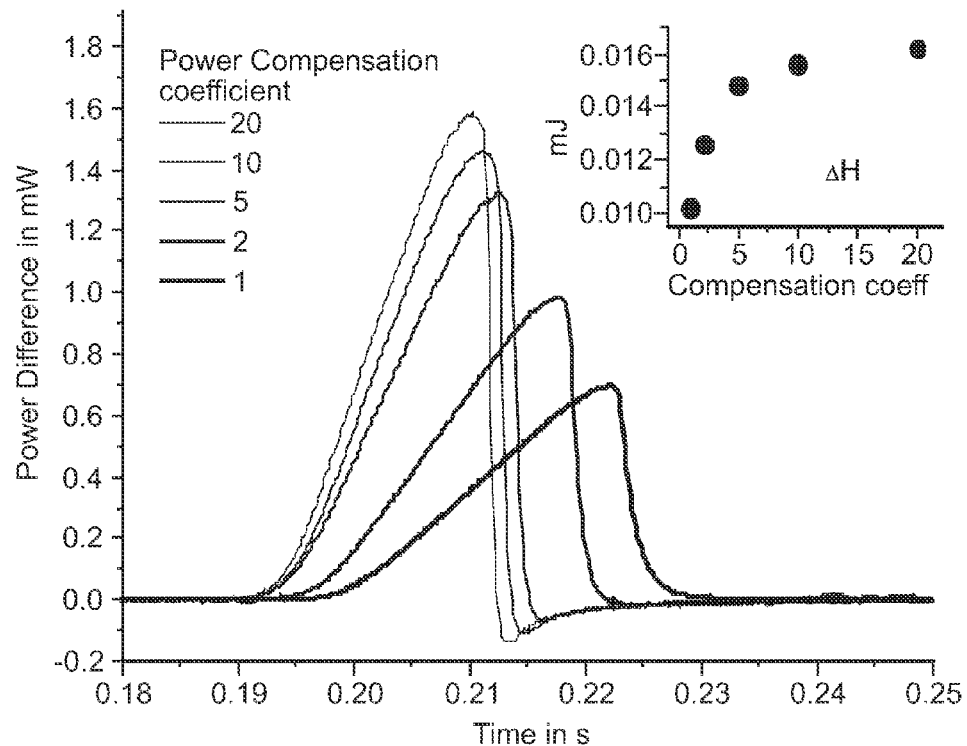

The effect of differential gain settings using the device of Example 1 was determined using about 350 micrograms of a tin sample, with the settings for the reference controller remaining constant. The single spherical particles were melted using a heating rate of 1,000 K/s and the different, differential gain settings. FIG. 10A shows the remaining temperature difference at different gains. FIG. 10B shows the power difference, calculated from the data shown in FIG. 10A. The inset of FIG. 10B shows the peak area as a function of gain setting. At low gain settings, the melting peak was much broader than for higher gain settings. Not enough heat was provided to the sample sensor, and consequently to the sample, allowing the sample to melt as fast as limited by the heat transfer (thermal resistor) between the sensor and the sample. Only at high gain settings was the limit reached, and a limiting shape of the peak is observed in FIG. 10A. At low gain settings, prerequisites for the power determination like equal temperature for reference and sample sensor are not fulfilled during melting. Therefore, the area (see inset of FIG. 10B), is smaller and reaches the true value only for gain settings above 10.

EXAMPLE 3

Polymer Testing

Figure 11A:
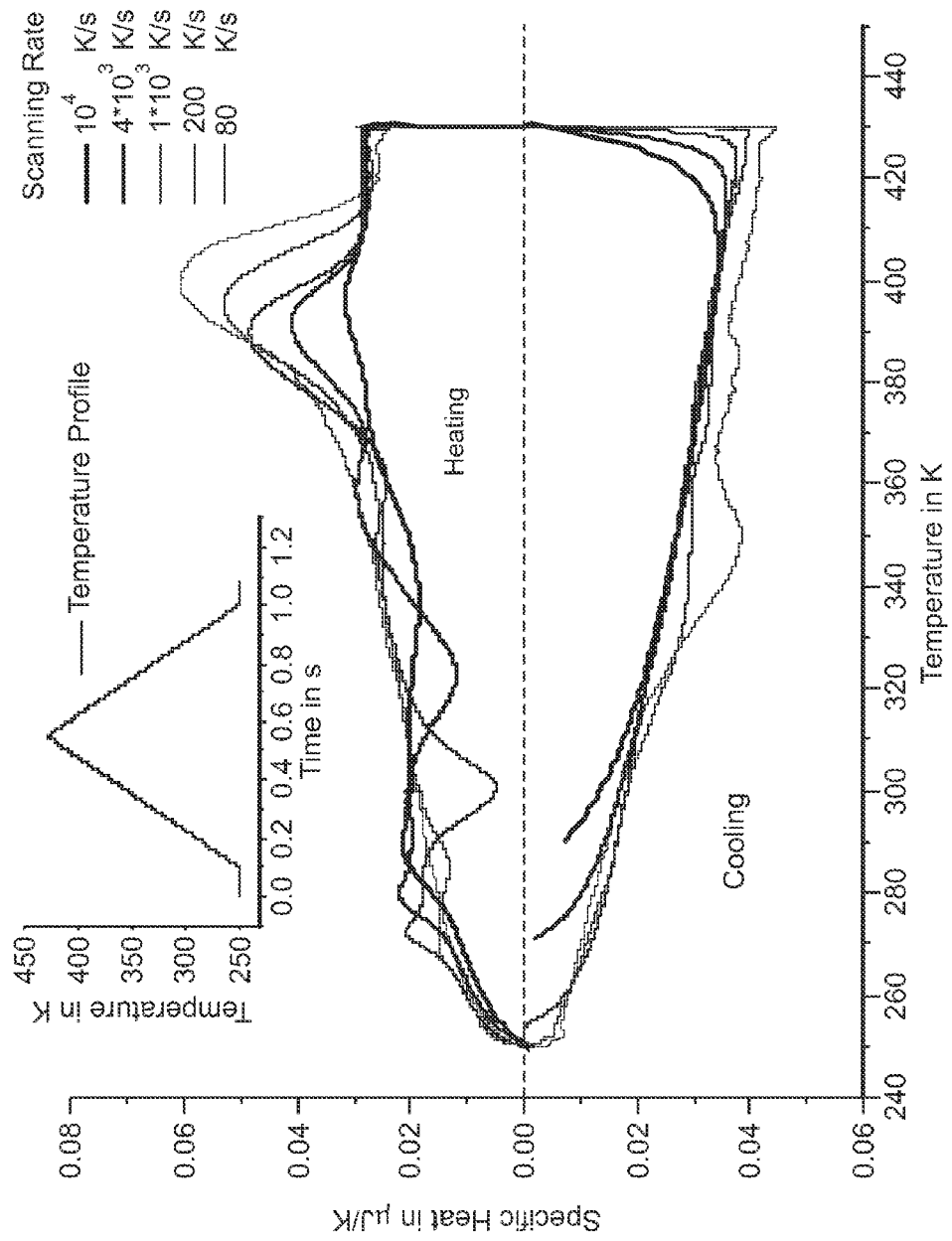
FIGS. 11A and 11B show the melting and cooling of a polymer, in accordance with certain examples.
Figure 11B:
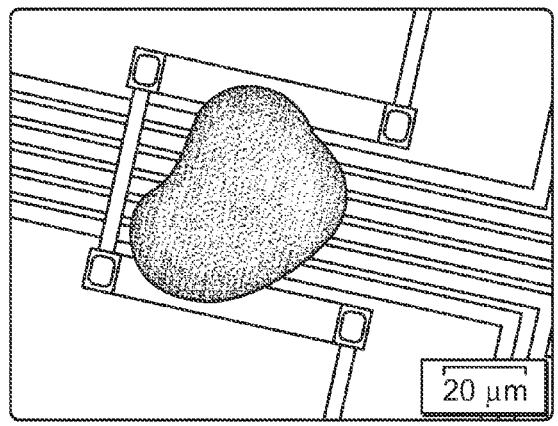

Polymers are known to show strong kinetic effects on crystallization and melting at high rates. An example of a polymer melting curve is shown in FIG. 11A. 20 nanograms of isotactic polypropylene (iPP), as shown deposited on the sensor in FIG. 11B, was melted and/or cooled at various rates. The inset of FIG. 11A shows the temperature profile. At rates below 200 K/second, crystallization was observed at cooling. The crystallization peak shifted to lower temperatures at increasing cooling rates and disappeared for rates above 200 K/s. On heating, cold crystallization was observed even at heating rates of 10,000 K/s. The glass transition at about 270 K as well as the cold crystallization shifted to higher temperatures with increasing heating rates. Only the position of the melting peak was more or less rate independent because of the very fast reorganization of the polymer crystals on heating. The rate independent position of the melting peak demonstrated that there was no significant thermal lag in the system; a consequence of the power compensation. As seen in FIG. 11A, the heat capacity values outside the transitions, for example, below glass transition and above melting, were basically rate independent. Thus, this example confirmed the device was working as intended.

Figure 12:
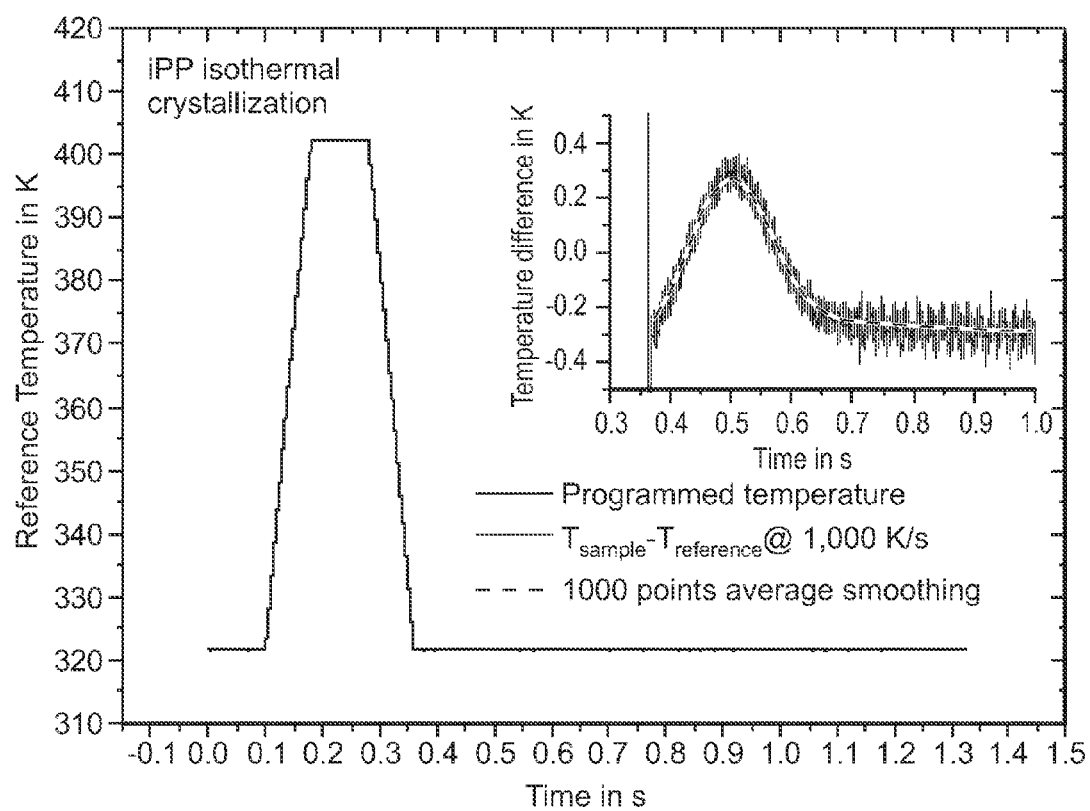
FIG. 12 shows the results of an isothermal crystallization experiment, in accordance with certain examples.

Because of the absence of any crystallization on cooling, isothermal crystallization experiments for isotactic polypropylene may be performed at any temperature. An example of this type of measurement is shown in FIG. 12. After a quench at 323 K at 1000 K/second, the temperature difference between the sample and reference sensors equilibrated within about five milliseconds. After that time, the exothermic crystallization process manifested itself as an increase in temperature of the sample sensor as shown in the inset of FIG. 12. Even though there was a temperature increase, the measurement can be considered as isothermal because the increase is only about 0.5 K or less.

The following articles are incorporated herein by reference for all purposes.

1. van Herwaarden A W. Overview of calorimeter chips for various applications. Thermochim Acta 2005:432(2):192-201.
2. Pijpers M F J, Mathot V B F, Goderis B, Scherrenberg R, van der Vegte E. High-speed calorimetry for the analysis of kinetics of vitrification, crystallization and melting of macromolecule. Macromolecules 2002:35(9):3601-3613.
3. Brucato V, Piccarolo S, La Carrubba V. An experimental methodology to study polymer crystallization under processing conditions. The influence of high cooling rates. Chem Eng Sci 2002:57(19):4129-4143.
4. O'Neill M J. The analysis of a temperature-controlled scanning calorimeter. Anal Chem 1964:36(7):1238-1245.
5. Watson E S, O'Neill M O, Justin J, Brenner N. A differential scanning calorimeter for quantitative differential thermal analysis. Anal Chem 1964:36(7):1233-1238.
6. Hager N E. Thin heater calorimeter. Rev Sci Instrum 1964: 35(5):618-624.
7. Allen L H, Ramanath G, Lai S L, Ma Z, Lee S, Allman D D J, Fuchs K P. 1000 000 "CIS thin film electrical heater: In situ resistivity measurements of and I TiISi thin films during ultra rapid thermal annealing. Appl Phys Lett 1994:64 (4):417-419.
8. Efremov M Y, Olson E A, Zhang M, Schiettekatte F, Zhang Z, Allen L H. Ultrasensitive, fast, thin-film differential scanning calorimeter. Rev Sci Instrum 2004:75(1):179-191.
9. Lopeandia A F, Valenzuela J, Rodríguez-Viejo J. Power compensated thin film calorimetry at fast heating rates. Sensors and Actuators A: Physical 2008:143(2):256-264.
10. Minakov A A, Schick C. Ultrafast thermal processing and nanocalorimetry at heating and cooling rates up to 1 MK/s. Rev Sci Instr 2007:78(7):073902-073910.
11. Adamovsky S A, Minakov A A, Schick C. Scanning microcalorimetry at high cooling rate. Thermochim Acta 2003:403(1):55-63.
12. De Santis F, Adamovsky S, Titomanlio G, Schick C. Scanning nanocalorimetry at high cooling rate of isotactic polypropylene. Macromolecules 2006:39:2562-2567.
13. Minakov A, Wurm A, Schick C. Superheating in linear polymers studied by ultrafast nanocalorimetry. Eur Phys J E Soft Matter 2007:23(1):43-53.
14. Tol R T, Minakov A A, Adamovsky S A, Mathot V B F, Schick C. Metastability of polymer crystallites formed at low temperature studied by Ultra fast calorimetry* Polyamide 6 confined in sub-micrometer droplets vs bulk PA6. Polymer 2006:47(6):2172-2178.
15. Minakov A A, Mordvintsev D A, Schick C. Melting and Reorganization of Poly(ethylene Terephthalate) on Fast Heating (1,000 K/s). Polymer 2004:45(11):3755-3763.
16. Minakov A A, Mordvintsev D A, Schick C. Isothermal reorganization of poly(ethylene terephthalate) revealed by fast calorimetry (1000 K s-1; 5 ms). Faraday Discuss 2005: 128:261-270.

When introducing elements of the examples disclosed herein, the articles "a," "an," and "the" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure. To the extent that the meaning of any terms in the publications incorporated herein by reference conflict with those used in the instant disclosure, the meaning of the terms in the instant disclosure are intended to be controlling.

What is claimed is:
1. A calorimeter comprising:
a thin film sample sensor;
a thin film reference sensor;
a first controller that receives a temperature signal from only the reference sensor and generates a first control signal, based on the received temperature signal, to provide average power to the sample sensor and to the reference sensor;
a second controller that receives temperature signals from both the sample sensor and the reference sensor and generates a second control signal, based on the temperature signals received from both the sample sensor and the reference sensor, to provide differential power to only the sample sensor; and
a storage medium configured with a temperature program with a selected heating rate of at least 10 Kelvin/second, wherein at least one of the first and second controllers is a proportional controller that detects temperature changes at a heating rate of 10 Kelvin/second or more.
2. The calorimeter of claim 1, in which the first controller is a proportional-integral-derivative controller.
3. The calorimeter of claim 2, in which the second controller is an analog proportional controller.
4. The calorimeter of claim 1, in which a cooling rate of the temperature program is at least 10 Kelvin/second.
5. The calorimeter of claim 1, in which each of the thin film sample sensor and the thin film reference sensor is a XI-296 sensor, a XI-270 sensor, a XI-272 sensor or a XI-292 sensor.
6. A control system for a calorimeter comprising a sample sensor and a reference sensor, the control system comprising:
a first controller that receives a temperature signal from only the reference sensor and generates a first control signal, based on the received temperature signal, to provide power to the sample sensor and to the reference sensor;
a second controller that receives temperature signals from both the sample sensor and the reference sensor and generates a second control signal to provide differential power to only the sample sensor; and
a storage medium configured with a temperature program with a selected heating rate of at least 10 Kelvin/second, wherein at least one of the first and second controllers is a proportional controller that detects temperature changes at a heating rate of 10 Kelvin/second or more.
7. The control system of claim 6, in which the first controller is a proportional-integral-derivative controller and the second controller is an analog proportional controller.
8. The control system of claim 7, in which the first controller and the second controller are configured to provide power to a thin film sample sensor and a thin film reference sensor.
9. The control system of claim 6, in which the second controller detects temperature changes at a heating rate of 10 Kelvin/second or more.
10. The control system of claim 6, in which the second controller is a proportional-integral-derivative controller.
11. A method of controlling a calorimeter that includes a reference sensor and a sample sensor, the method comprising:

generating a first control signal using a first controller, the first control signal based on receipt of a temperature signal from only the reference sensor of the calorimeter by the first controller;

providing power to the reference sensor and the sample sensor, based on the generated first control signal, to control the average temperature of the reference sensor and the sample sensor;

generating a second control signal using a second controller, the second control signal based on receipt of a temperature signal from each of the reference sensor and the sample sensor to provide a differential temperature between the reference sensor and the sample sensor;

storing a temperature program with a selected heating rate of at least 10 Kelvin/second; and providing differential power to only the sample sensor, based on the generated second control signal, to heat or cool the temperature of the sample sensor to substantially the same temperature as the reference sensor, wherein at least one of the first and second controllers is a proportional controller that detects temperature changes at a heating rate of 10 Kelvin/second or more.

12. The method of claim 11, further comprising configuring the first controller to be a proportional-integral-derivative controller.

13. The method of claim 12, further comprising configuring the second controller to be a proportional-integral-derivative controller.

14. The method of claim 11, further comprising heating the sample sensor and the reference sensor at a heating rate of 10 Kelvin/second or more.

15. The method of claim 11, in which the second controller is an analog proportional controller.

16. A method of facilitating calorimeter control, the method comprising:

providing a control module comprising:

a first controller that receives a temperature signal from only a reference sensor and generates a first control signal, based on the received temperature signal, to provide average power to a sample sensor and to the reference sensor, and a second controller that receives temperature signals from both the sample sensor and the reference sensor and generates a second control signal, based on the temperature signals received from both the sample sensor and the reference sensor, to provide differential power to only the sample sensor; and a storage medium configured with a temperature program with a selected heating rate of at least 10 Kelvin/second, wherein at least one of the first and second controllers is a proportional controller that detects temperature changes at a heating rate of 10 Kelvin/second or more.

* * * * *